United States Patent [19]

Katayama et al.

[11] Patent Number: 4,963,451
[45] Date of Patent: Oct. 16, 1990

[54] 1,2,4,5-BENZOYLENEBIS(ANTHRAQUINONE[1,2-d]IMIDAZOLE) COMPOUNDS AND PHOTOSENSITIVE MEMBERS CONTAINING THEM

[75] Inventors: Satoshi Katayama, Tenri; Yoshihide Shimoda, Nara; Hiroshi Sugimura, Habikino; Eiji Imada, Nara; Shuhei Tsuchimoto, Nara, all of Japan

[73] Assignee: Sharp Kabushiki Kaisha, Osaka, Japan

[21] Appl. No.: 410,890

[22] Filed: Sep. 22, 1989

Related U.S. Application Data

[62] Division of Ser. No. 280,972, Dec. 7, 1988, Pat. No. 4,908,457.

[30] Foreign Application Priority Data

Dec. 8, 1987 [JP] Japan .................... 62-310466

[51] Int. Cl.$^5$ ...................... G03G 15/05; G03G 15/06
[52] U.S. Cl. ........................ 430/72; 548/324
[58] Field of Search ........................... 430/72

[56] References Cited

U.S. PATENT DOCUMENTS 3,560,360  2/1971  Carreira et al. ............... 430/72
4,752,561  6/1988  Nishijima et al. ............. 430/551

Primary Examiner—Marion C. McCamish
Assistant Examiner—S. C. Crossan
Attorney, Agent, or Firm—Birch, Stewart, Kolasch & Birch

[57] ABSTRACT 1,2,4,5-Benzoylenebis(anthraquinone[1,2-d]imidazole) compounds represented by following general formula (1) or (2)

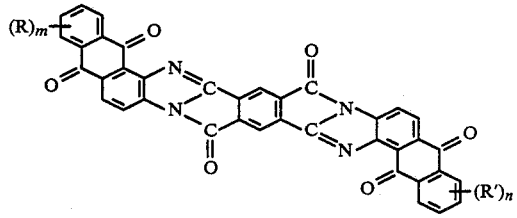

(1)

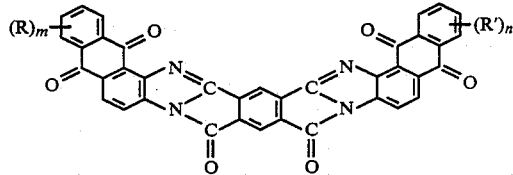

(2)

wherein R and R' each are hydrogen atom, a halogen atom, hydroxyl group, a lower alkyl group, a lower alkoxy group or an aryl group which may be substituted and m and n each are an integer of 1 or 2, and photosensitive members for electrophotography having a photosensitive layer containing them.

10 Claims, 1 Drawing Sheet

1,2,4,5-BENZOYLENEBIS(ANTHRAQUINONE[1,2-d]IMIDAZOLE) COMPOUNDS AND PHOTOSENSITIVE MEMBERS CONTAINING THEM

This application is a divisional of copending application Ser. No. 280,972, filed on Dec. 7, 1988, now U.S. Pat. No. 4,908,457.

BACKGROUND OF THE INVENTION

1. Field of the Invention

The present invention relates to novel imidazole compounds and photosensitive members utilizing them. More particularly, it relates to novel 1,2,4,5-benzoylenebis (anthraquinone[1,2-d]imidazole) compounds, which are organic photoconductive substances, and photosensitive members for electrophotography having a photosensitive layer containing the novel compounds.

2. Description of the Prior Art

Generally, an electrophotography using a photoconductive photosensitive member is one of information recording means utilizing photoconductive phenomena.

In the electrophotography, the surface of the photosensitive member is uniformly charged by a corona discharge or the like, in darkness and then, by subjecting the charged surface to image exposure, the electric charge of the exposed portion is discharged selectively to form an electrostatic latent image at the unexposed portion of the surface. Next, the latent image is converted to a visual image by allowing charged colored fine particles (toner) to adhere to the latent image by means of electrostatic attraction force, etc., whereby an image is formed. The basic properties required for photoconductive photosensitive members used in the electrophotography technics of these serial processes are:

(1) that the photosensitive members can be electrified in darkness at a suitable electric potential uniformly, (2) that they have a high, electric charge-retentivity in darkness and discharge of the electric charge from them is minor, (3) that they are superior in photosensitivity and quickly discharge the electric charge by photoirradiation, and the like. Moreover, it is required for the photoconductive photosensitive members to have good stability and endurance; such as, that the surface of them can be discharged easily, with a minor residual electric potential on the surface, that they have mechanical strength and are superior in flexibility, that their electric properties, especially, electrification property, remaining electric potential, etc., do not fluctuate even when they are used repeatedly, that they are resistant to heat, light, temperature, humidity, ozone deterioration, etc., and the like.

Photosensitive members for electrophotography now used practically may be divided broadly into two groups, one utilizing materials of inorganic series and one utilizing materials of organic series.

As representative photosensitive members of inorganic series, there can be mentioned those of selenium series, such as amorphous selenium (a-Se), amorphous arsenic selenide (a-As$_2$Se$_3$), etc., those comprising color-sensitized zinc oxide (ZnO) or cadmium sulfide (CdS) dispersed in a bonding resin, those using amorphous silicon (a-Si), and the like. As representative photosensitive members of organic series, there are those using a charge-transfer complex of 2,4,7-trinitro-9-fluorenone (TNF) and poly-N-vinylcarbazole (PVK), and the like.

These photosensitive members have many merits, but at the same time some demerits. For instance, photosensitive members of selenium series and photosensitive members using CdS have some questions in respect of their heat-resistance and can-stability. Moreover, there is a restriction in the use of those photosensitive members that, because of their toxicity, they cannot be simply thrown away but have to be recovered. Photosensitive members comprising ZnO dispersed in resin are now practically not used, because of their low sensitivity and inferior endurance. Amorphous silicon photosensitive members having merits, such as high sensitivity, high endurance, etc., have also problems that their manufacturing cost is high because of their complicated manufacturing process, that they give faulty images resulting from the fault of membrane which is inherent in amorphous silicon, and the like. Further, they have defects that their flexibility is not a satisfactory one, that their processing into various forms such as drum, sheet, etc., is not easy, and the like.

On the other hand, attention is given to organic photosensitive members as the most important ones, because suitable organic materials without the problems on canstability and toxicity can be selected from existing various materials or organic materials having improved durability and low cost become available. However, there remains another disadvantage on sensitivity of organic photosensitive materials to be improved. The above described PVK-TNF charge-transfer complex series resulted from such improvement, but did not attain sufficient sensitivity. In addition, various sensitizing methods have been proposed. At present, the main current of organic photosensitive members practically used is occupied by laminate type photosensitive members (hereinafter, called "multilayer type photosensitive members") having a superior sensitizing property, which comprise a layer (hereinafter, called "charge-generating layer") containing a substance which allows generation of charge-carriers by photoirradiation (hereinafter, called "charge-generating substance") and a layer (hereinafter, called "charge-transporting layer") consisting mainly of a substance which accepts and transports the charge carriers generating in the charge-generating layer (hereinafter, called "charge-transporting substance").

As organic materials which may be used for the charge-generating layer of the above-mentioned multilayer type photosensitive members, bis-azo pigments such as chlorodianblue, etc., polycyclic quinone series pigments such as dibromoanthanthrone, etc., perillene, quinacridone or phthalocyanine series compounds, azulenium salt compounds, and the like, are known. However, some of these charge-generating materials are lacking in photoconductivity though they have a good absorption spectral property for photosensitive members, in the visual ray region, and some of them have an absorption spectral property not suitable for photosensitive members though they have a good photoconductivity. Thus, it was very difficult to compose a photosensitive members having a good sensitivity, by striving for coexistence of the absorption spectral property and the photoconductivity. The multilayer type photosensitive members provided with such charge-generating layer which have been hitherto proposed are, for example, (1) those wherein a thin layer formed by application of an organic amine solution of chlorodianblue is used as the charge-generating layer and a hydrazone compound is used as the charge-transporting substance of the charge-transporting layer (Japanese Patent Publication No. SHO 55-42380 is referred to), (2) those wherein a bis-azo compound is used as the charge-generating substance of the charge-generating layer and a hydrazone compound is used as the charge-transporting layer (Japanese Patent Application Laid-open No. SHO 59-214035 is referred to), (3) those wherein an azulenium salt compound is used as the charge-generating substance of the charge-generating layer and a hydrzaone compound or the like is used as the charge-transporting layer (Japanese Patent Application Laid-open No. SHO 59-53850 is referred to), (4) those wherein a perillene derivative is used as the charge-generating substance of the charge-generating layer and an oxadiazole derivative is used as the charge-transporting layer (U.S. Pat. No. 3871882 is referred to), and the like.

However, these photosensitive members (1)-(4) were still insufficient in sensitivity, as they were used practically. Moreover, these hitherto known multilayer type photosensitive members had a problem in their stability as they were used repeatedly.

Therefore, notwithstanding the above-mentioned many merits of the organic photoconductive substances, compared with inorganic ones, they were not so much used for photosensitive members for electrophotography because photosensitive members using them were inferior in sensitivity and endurance.

The present invention has been made in view of the above-described circumstances and its purpose resides in providing organic photosensitive members for electrophotography having a high sensitivity and a superior stability on repeated use.

As a result of keen investigations for organic photoconductive substances having a high sensitivity and a high endurance, which have been performed from the above-described view-points, the inventors of the present invention have found that a specific group of novel imidazole compounds which were not yet disclosed in the literature are suitable as the organic photoconductive substances. Thus, the present invention has been completed.

SUMMARY OF THE INVENTION

The present invention provides 1,2,4,5-benzoylenebis(anthraquinone[1,2-d]imidazole) compounds represented by the following formula (1) or (2):

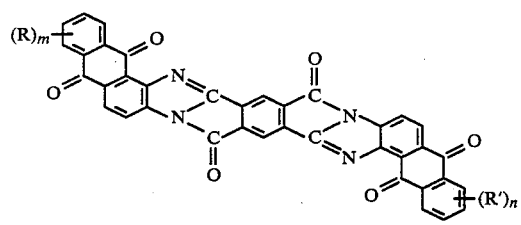

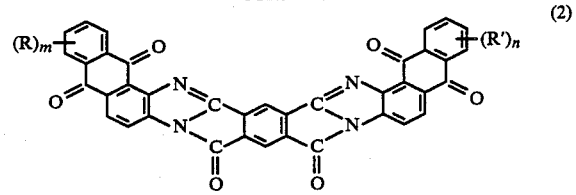

wherein R and R' each is hydrogen atom, a halogen atom, hydroxyl group, an alkyl group which may be substituted, an alkoxy group which may be substituted or an aryl group which may be substituted, independently, and m and n each is an integer of 1 or 2, and photosensitive members having a photosensitive layer containing them.

The photosensitive members using the imidazole compounds of the present invention have a high sensitivity and show only a minor change or fluctuation in sensitivity and chargeability, as they are used repeatedly, that is, they are superior also in endurance.

The photosensitive members containing the imidazole compounds represented by the general formulae (1) and (2) of the present invention exhibit an excellent performance, especially as photosensitive members for electrophotography. Further, they can be used not only in the field applying electrophotography, such as laser printers, CRT printers, etc., besides copying machines, but also widely for a solar battery, a photosensor, etc.

DESCRIPTION OF THE PREFERRED EMBODIMENTS

Figure 1:
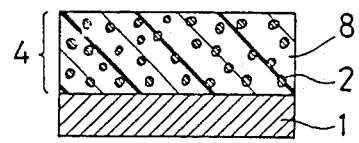
FIGS. 1-8 are each an enlarged sectional diagram showing an Example of the photosensitive members of the present invention.

The 1,2,4,5-benzoylenebis(anthraquinone[1,2-d]imidazole) compounds of the present invention (hereinafter, called the imidazole compounds of the present invention) are represented by the above-described general formula (1) or (2).

In the general formulae (1) and (2), R and R' each are hydrogen atom, a halogen atom, hydroxyl group or an alkyl group, an alkoxy group or an aryl group which may be substituted, the R and R' may be identical with or different from each other, and m and n each are an integer of 1 or 2.

Examples of the halogen atoms are a fluorine atom, chlorine atom, bromine atom and iodine atom; the alkyl group may be straight or branched chain lower alkyl groups having from one to five carbon atoms, such as methyl group, ethyl group, propyl group, isopropyl group, etc.; and the alkoxy group may be lower alkoxy groups having from one to five carbon atoms, such as methoxy group, ethoxy group, propoxy group, isopropoxy group, etc. Further, examples of the aryl groups are phenyl group, naphthyl group, etc.

Examples of the substituents for the aryl groups are a lower alkyl group, such as methyl group, ethyl group, etc.; a halogen atom, such as fluorine atom, chlorine atom, bromine atom or iodine atom; nitro group; cyano group; a lower alkoxy group, such as methoxy group or ethoxy group, etc.; a di-lower alkylamino group, such as dimethylamino group or diethylamino group. They may be substituted not only by one of these substituents, but also by two or more of these substituents. Chlorine atom or nitro group is preferable as the substituents.

The imidazole compounds of the present invention may be prepared by utilizing of publicly known processes. For example, they may be prepared by treating pyromellitic anhydride of the following formula (3) with an aromatic diamine of the following general formulae (4) and (5) (wherein, R, R', m and n have the same meaning as defined in the formulae (1) and (2)) in an inert solvent, at an elevated temperature, preferably at 100–350° C., particularly at a temperature higher than 200° C. The reaction is performed until its completion. A reaction time of 3–24 hours is usually preferred (Bull. Chem. Soc. Japan, 25, 411–413 (1952); ibid. 27, 602–605 (1954) are refferred to).

Examples of the inert solvent are nitrobenzene, an aprotic polar solvent, such as N-methylpyrrolidone, N,N-dimethylformamide, N,N-dimethylacetamide, etc., a basic solvent, such as quinoline, etc., or a chlorine-series solvent, such as o-dichlorobenzene, etc., or in a mixture of these solvents.

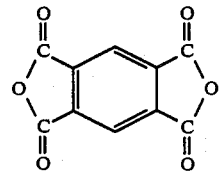

[3]

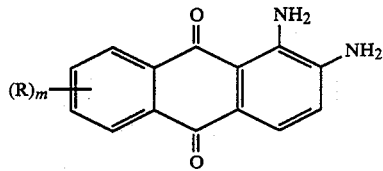

[4]

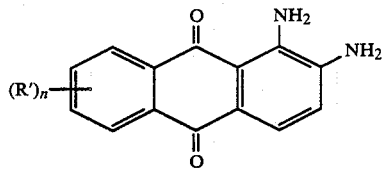

[5]

The photosensitive layers of the present invention may contain two or more kinds of the imidazole compounds of the present invention represented by the above general formula (1) or (2).

Preferred imidazole compounds of the general formula (1) or (2) of the present invention are shown:

| Compound No. | |
|---|---|
| 1. | 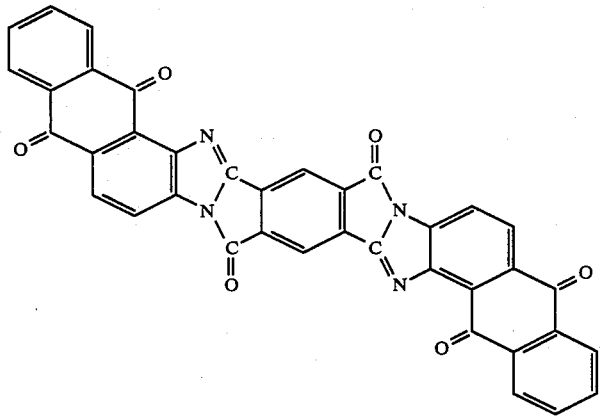 |
| 2. | 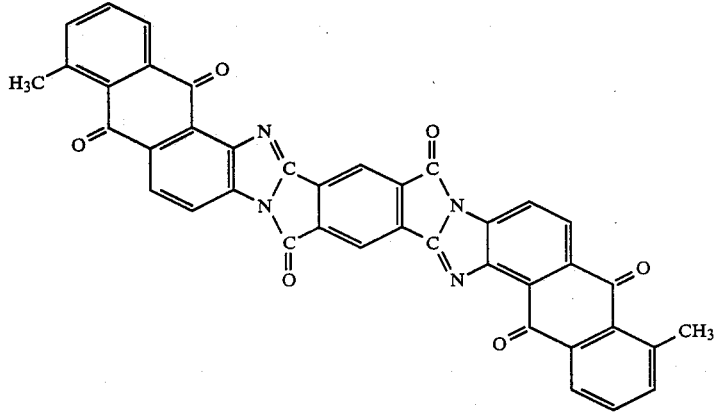 |

-continued
| Compound No. | |
|---|---|
| 3. | 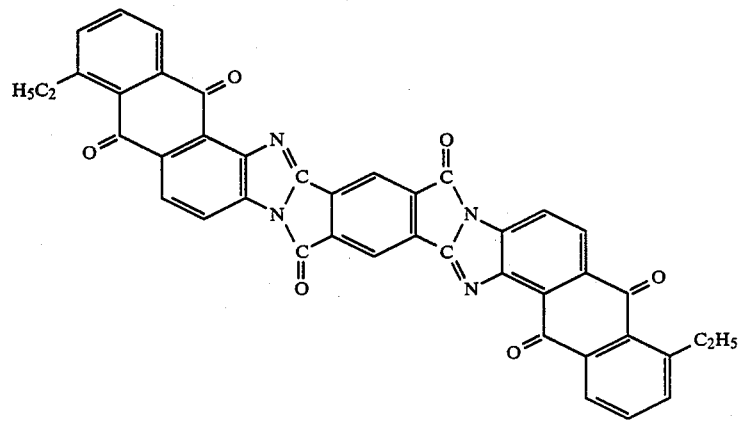 |
| 4. | 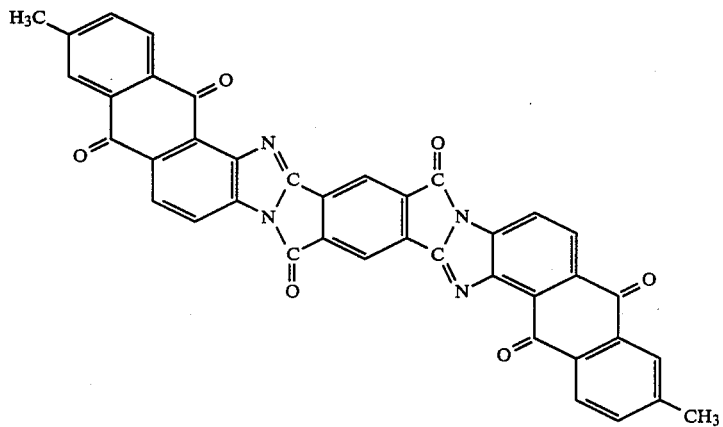 |
| 5. | 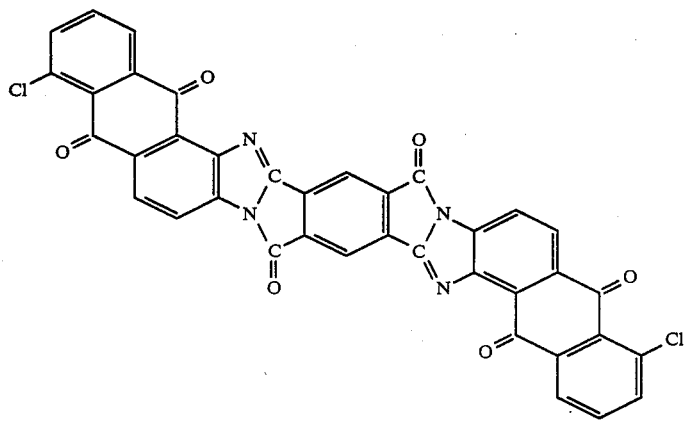 |

-continued
Compound
No.
6.
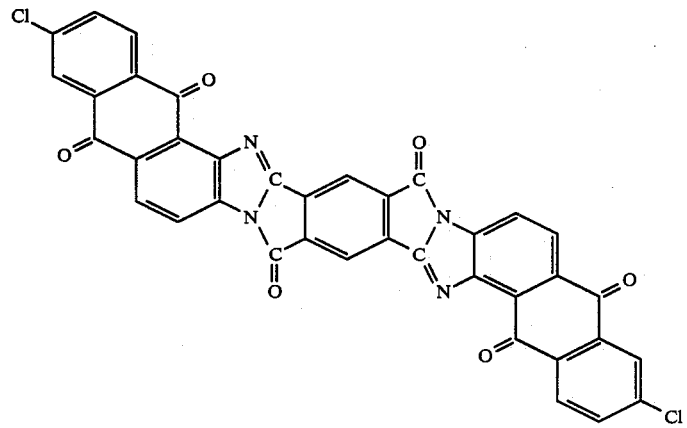
7.
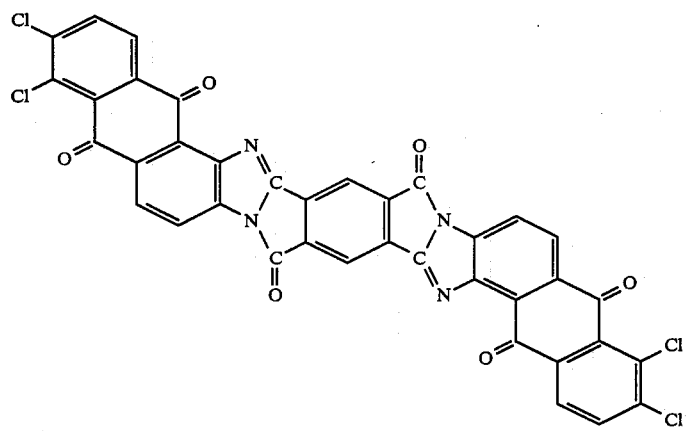
8.
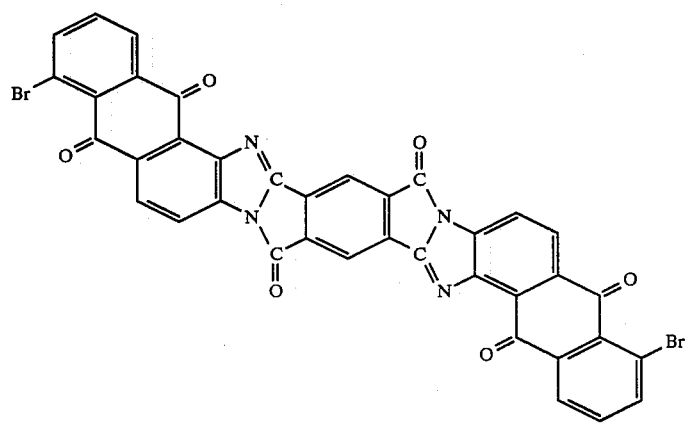

-continued
| Compound No. | |
|---|---|
| 9. | 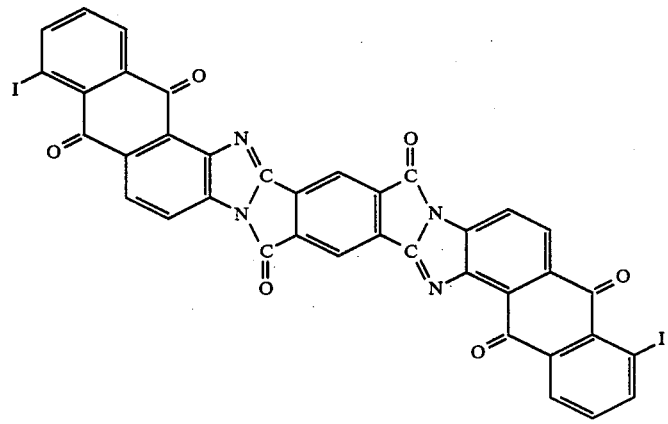 |
| 10. | 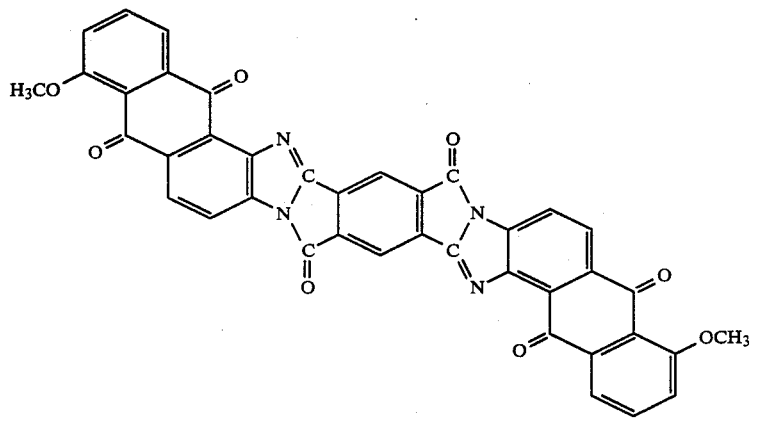 |
| 11. | 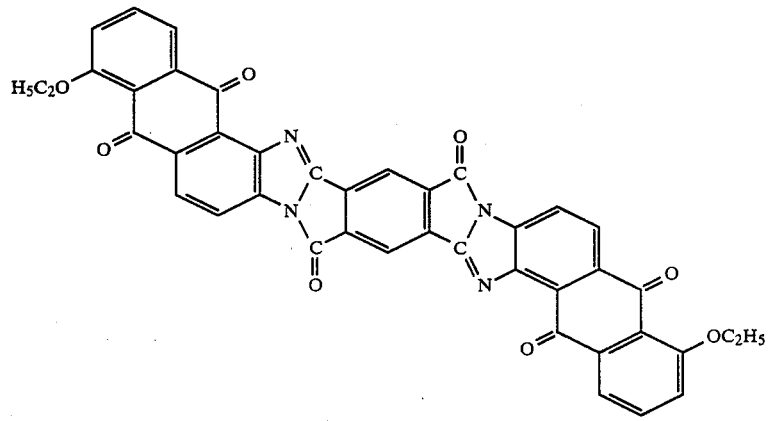 |

| Compound No. | |
|---|---|
| 12. | 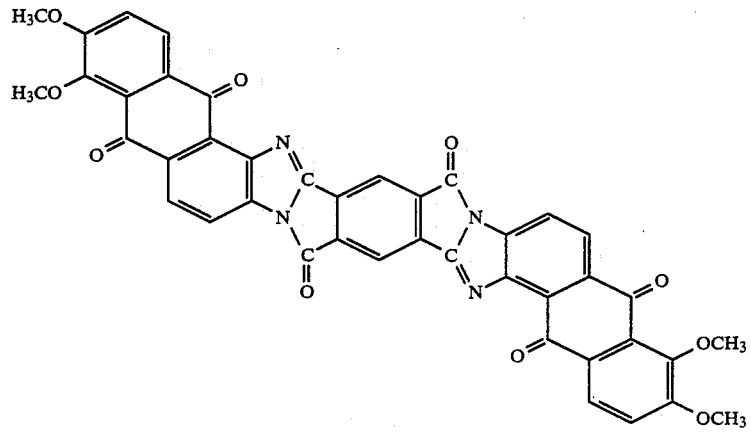 |
| 13. | 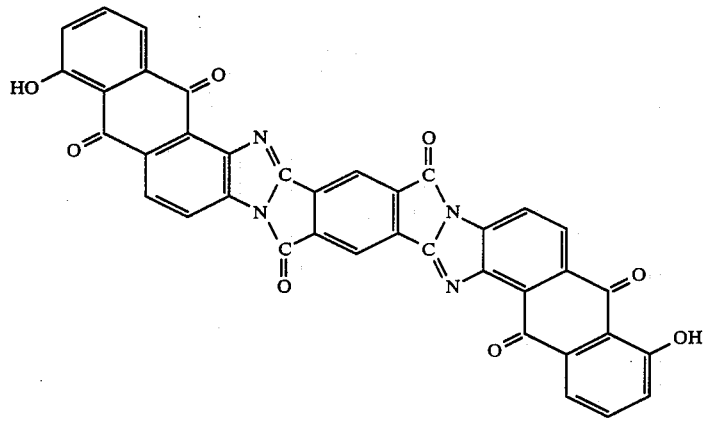 |
| 14. | 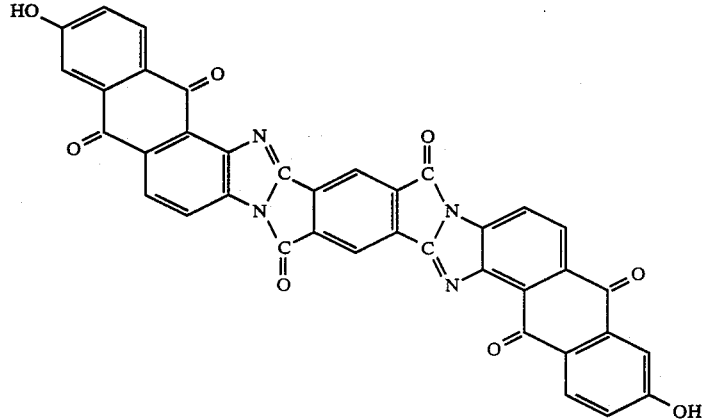 |

| Compound No. | |
|---|---|
| 15. | 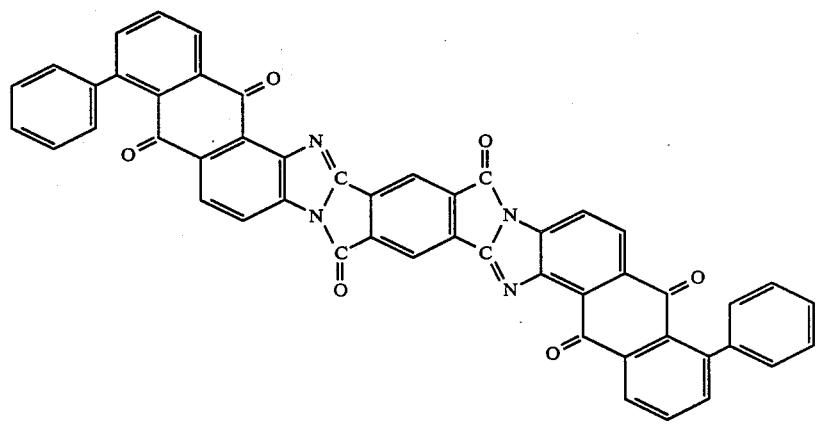 |
| 16. | 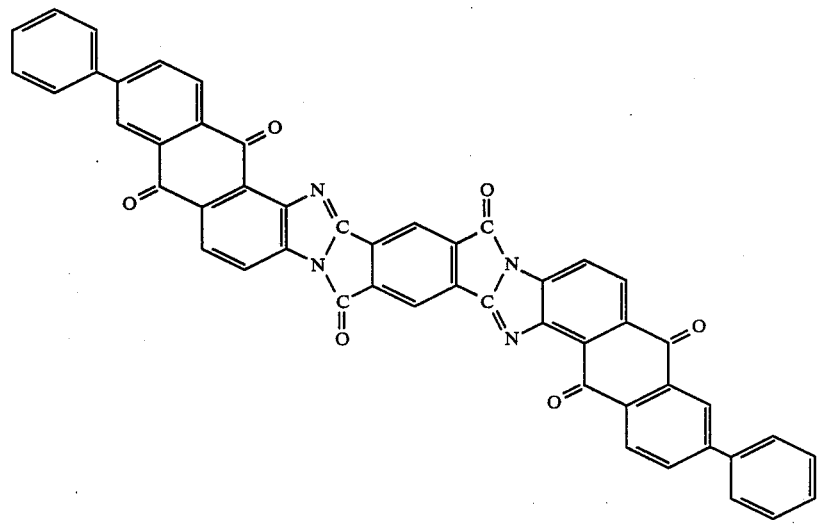 |
| 17. | 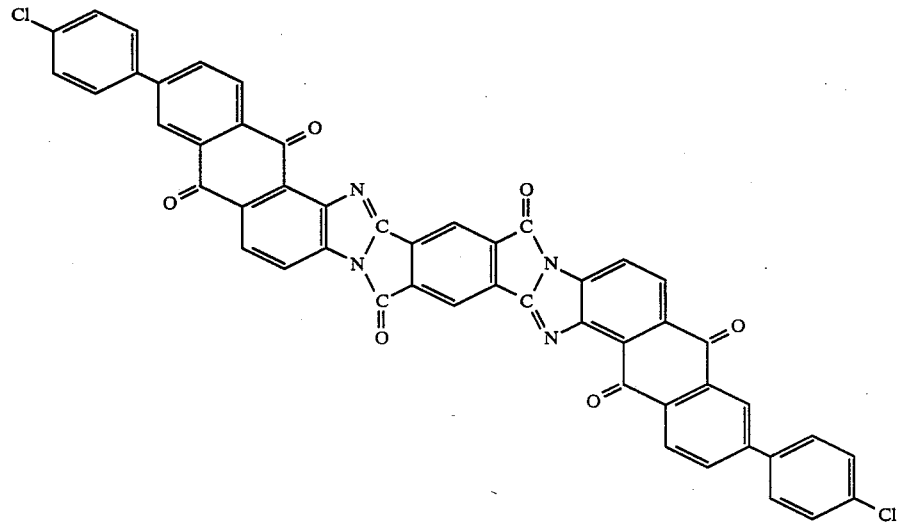 |

| Compound No. | |
|---|---|
| 18. | 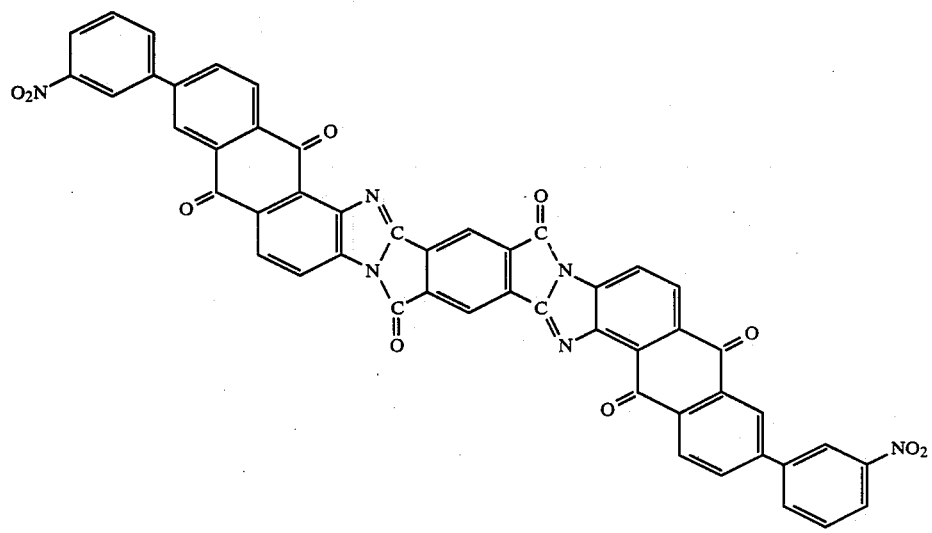 |
| 19. | 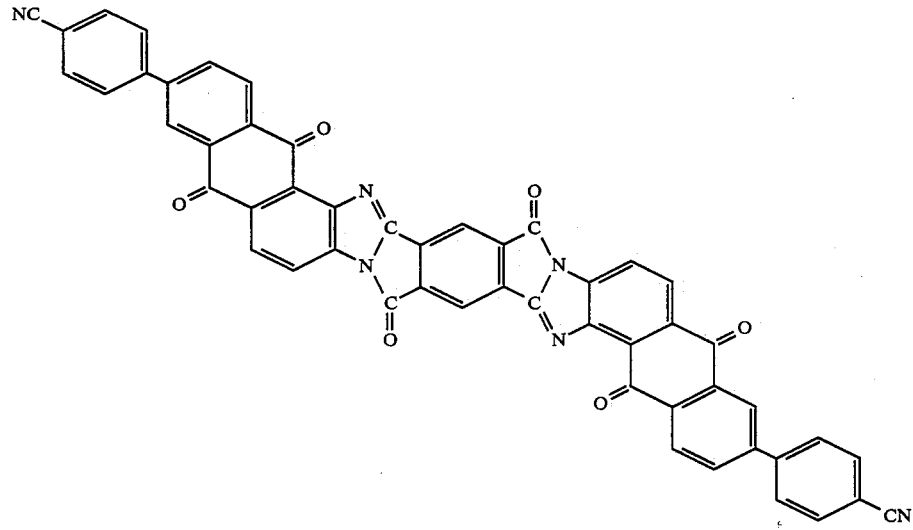 |
| 20. | 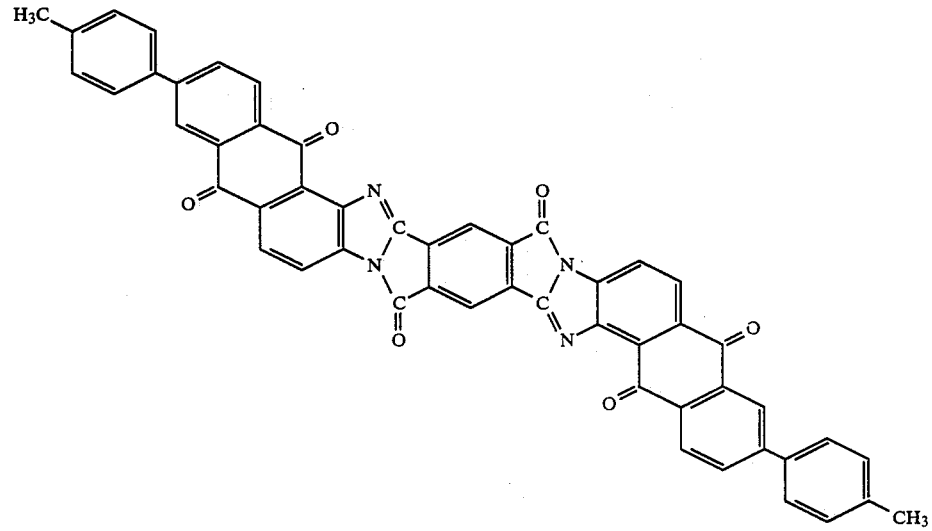 |

| Compound No. | |
|---|---|
| 21. | 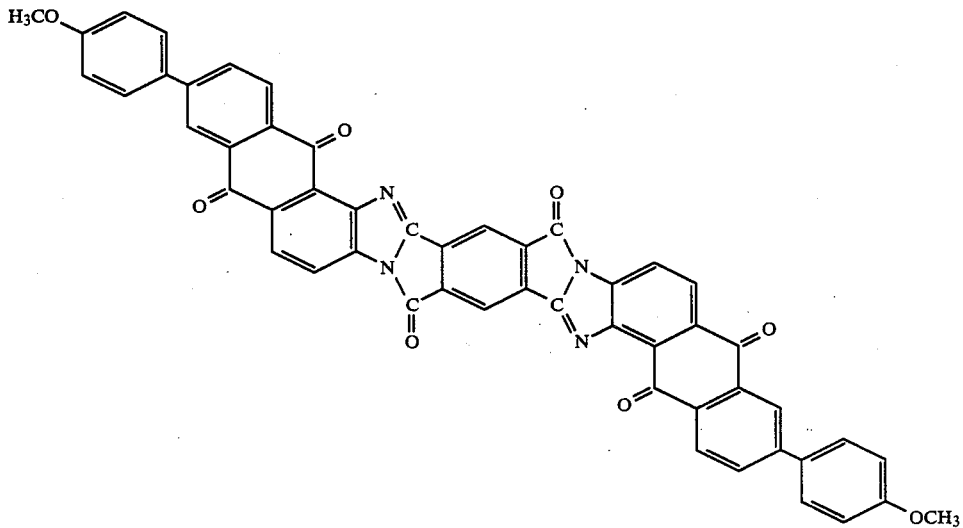 |
| 22. | 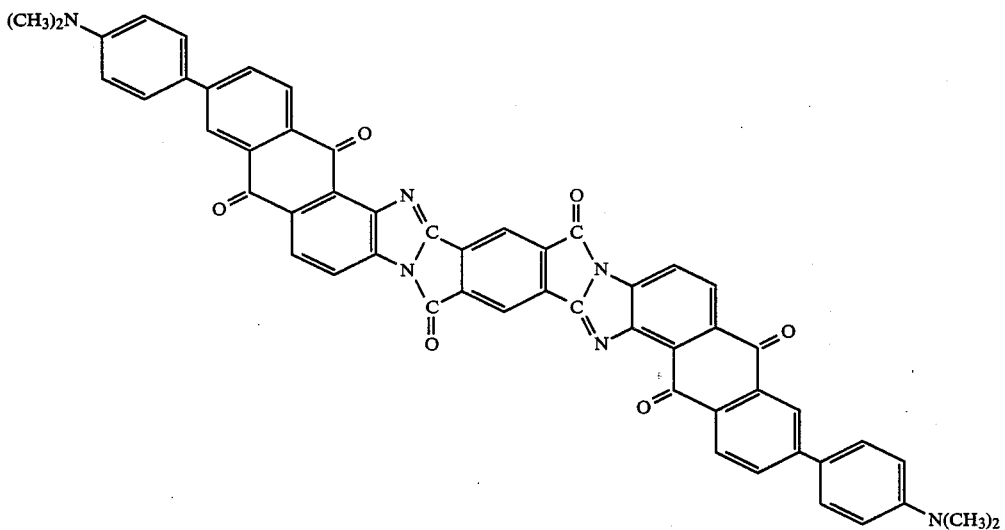 |
| 23. | 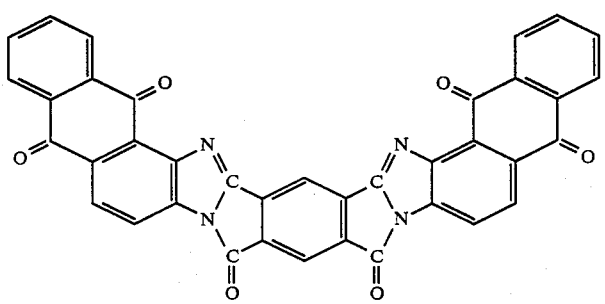 |

-continued

| Compound No. | |
|---|---|
| 24. | 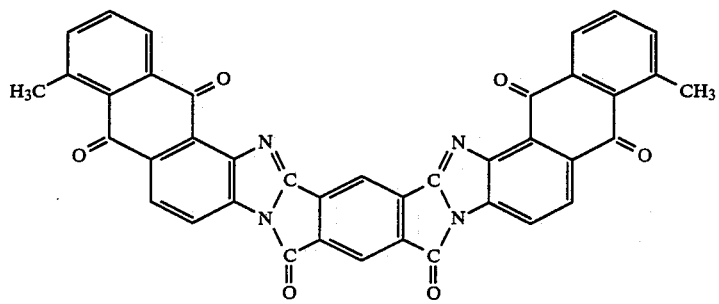 |
| 25. | 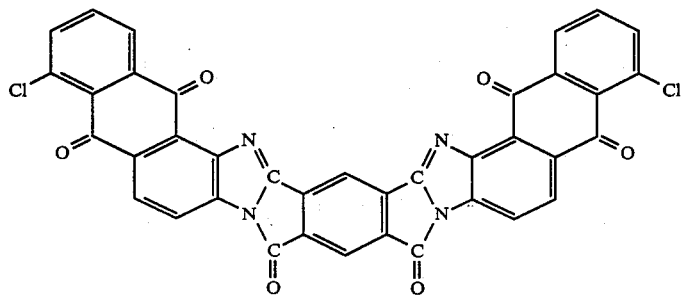 |
| 26. | 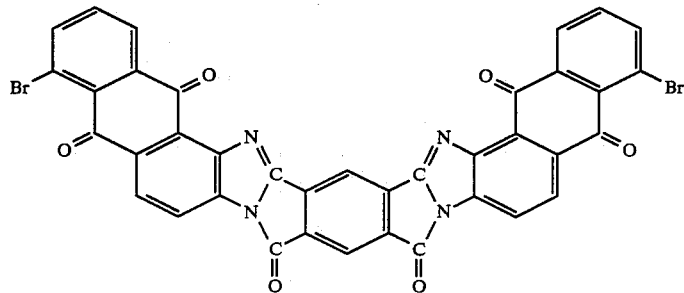 |
| 27. | 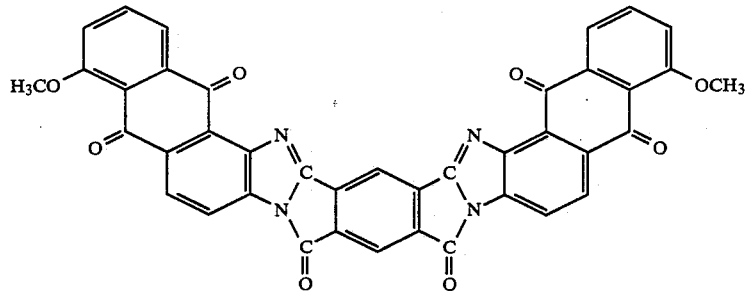 |

The imidazole compounds of the present invention have photoconductivity, and so, when photosensitive members for electrophotography are prepared using them, various types of photosensitive layers may apply. For example, the imidazole compounds of the present invention may be dispersed in a polymer binder and applied on a conductive support to make a photosensitive layer. In another process, the imidazole compounds of the present invention may be utilized as a charge-generating substance, since their charge-generating ability is especially superior among their photoconductive properties. That is, the imidazole compounds may be dispersed in a binder polymer containing a charge-transporting substance (the binder polymer is not necessarily used when the charge-transporting substance has a coating membrane-forming ability), to form a photosensitive layer. Further, it may be used to prepare the so-called multilayer type photosensitive members for electrophotography having a multilayer type photosensitive layer which comprises a laminate of a charge-generating layer containing the imidazole compounds and a charge-transporting layer.

Usable above-mentioned conductive supports are those substrates which per se have conductivity, such as aluminum, aluminum alloy, copper, zinc, stainless steel, nickel, chromium, titanium, etc., plastics having a conductive coating membrane layer formed by a vacuum evaporation method or the like, of aluminum, aluminum alloy, indium oxide or tin oxide, substrates comprising plastics, paper, or the like, impregnated with conductive particles or plastics having conductive polymers.

Figure 2:
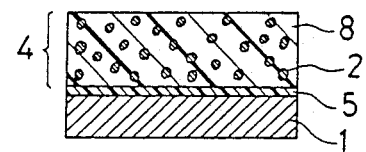
Figure 3:
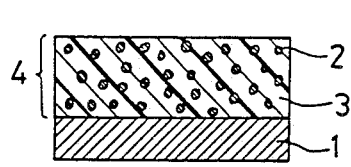
Figure 4:
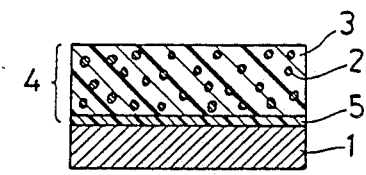
Figure 5:
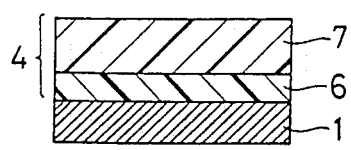

FIGS. 1-8 show each a representative form of the photosensitive members for electrophotography of the present invention. In the photosensitive members of FIG. 1 and FIG. 2, the imidazole compounds of the present invention act as a photoconductor, and the charge-generation and the charge-transportation are effected through the intermediation of the imidazole compounds. In the FIG. 1 and FIG. 2, 1 denotes a conductive support, 2 denotes the imidazole compound, 4 denotes a photosensitive layer, 5 denotes an undercoating layer and 8 denotes a binder. In FIG. 3 and FIG. 4 are shown those photosensitive members in which a photosensitive layer 4 comprising a dispersion of the imidazole compound 2 as the charge-generating substance in a charge-transporting substance-containing layer 3 is provided directly or through an undercoating layer 5 on a conductive support 1. As shown in FIG. 5-FIG. 8, a multilayer type photosensitive layer 4 comprising a laminate of a charge-generating layer 6 consisting mainly of the imidazole compound of the present invention, as the charge-generating substance, and a charge-transporting layer 7 consisting mainly of a charge-transporting substance, may be provided on a conductive support 1 to prepare photosensitive members. An undercoating layer 5 may be interposed between the conductive support 1 and the photosensitive layer 4, also in these cases. Further, as shown in FIG. 5 and FIG. 6 or FIG. 7 and FIG. 8, when the photosensitive layer 4 is composed of two layers, either of the charge-generating layer 6 and the charge-transporting layer 7 may be the upper layer. With a multi-layer type photosensitive member having a photosensitive layer 4 composed of two layers, especially superior photosensitive members for electrophotography are obtained.

The imidazole compounds of the present invention constituting the photosensitive layer 4 of laminate type may form the charge-generating layer 6 on the conductive support 1 or on the charge-transporting layer 7, directly or through an intermediate layer such as the undercoating layer 5, etc. The forming of such charge-generating layer is effected by vacuum evaporation of an imidazole compound of the present invention as the charge-generating substance, or by application of a dispersion obtained by dispersing an imidazole compound of the present invention in a suitable solvent and, if necessary, mixing with a binder, or of a dispersion obtained by dispersing an imidazole compound of the present invention in a suitable solvent containing a binder dissolved therein. Generally speaking, the latter method is preferred.

When the charge-generating layer is prepared by application method, dispersion of the imidazole compound in a binder solution can be performed efficiently by using ball mill, sand mill, roll mill, attritor, vibration mill, supersonic disperser, etc., and application of the dispersion can be performed efficiently by using air doctor coater, blade coater, spray coater, hot coater, squeeze coater, etc.

As the binder used here, there can be mentioned, for example, those insulating resins, such as polycarbonate resin, acrylic resin, polyester resin, polystyrene resin, melamine resin, silicone resin, polyvinyl butyral resin, polyamide resin, a copolymer resin containing two or more of the recurring units of the foregoing resins, such as vinyl chloride/vinyl acetate copolymer resin, acrylonirile/styrene copolymer resin, etc., and the like. However, the binder is not limited to these insulating resins, but any of generally used resins can be used solely or as a mixture of two or more of them.

Further, as the solvent for dissolving the binder used, can be used, for example, alcohols such as methanol, ethanol, isopropanol, etc., ketones such as acetone, methyl ethyl ketone, cyclohexanone, etc., esters such as ethyl acetate, butyl acetate, etc., ethers such as tetrahydrofuran, dioxane, etc., aromatic hydrocarbons such as benzene, toluene, xylene, etc., non-protonic polar solvents such as N,N-dimethylformamide, N,N-dimethylacetamide, dimethyl sulfoxide, etc., and the like.

The membrane thickness of the charge-generating layer 6 thus formed is suitably 0.01-20 $\mu$m, preferably 0.05-5 $\mu$m, more preferably 0.1-2 $\mu$m. Further, it is necessary to granulate the imidazole compound 2 of the present invention into fine particles having a particle size of 5 $\mu$m or less, preferably 3 $\mu$m or less, most preferably 1 $\mu$m or less. The binder resin contained in the charge-generating layer is suitably 80% by weight or less, preferably 40% by weight or less.

The charge-transporting layer 7 is electrically connected with the charge-generating layer 6 and has a function of transporting the charge carriers poured in from the charge-generating layer, in the presence of electric field. As materials for such charge-transporting layer, though the materials are generally classified into electrontransporting substances and hole-transporting substances, both of the two, and also a mixture of the two, can be used for the photosensitive layer of the present invention. As the electron-transporting substances, those substances having electron attractive groups such as nitro group, cyano group, etc., for example, nitrated fluorenones such as 2,4,7-trinitro-9-fluorenone, 2,4,5,7-tetranitro-9-fluorenone, etc., trinitrotoluene, and the like, are mentioned. As the hole-transporting substances, electron donative substances, for example, heterocyclic compounds such as carbazole, oxazole, thiazole, oxadiazole, imidazole, pyrazoline, etc., low molecular charge-transporting substances such as aniline derivatives, arylamine derivatives, hydrazone derivatives, etc., high molecular charge-transporting substances such as poly-N-vinylcarbazole, halogenated poly-N-vinylcarbazole, polyvinyl pyrene, polyvinyl anthracene, etc., and the like, may be used. However, the charge-transporting substances applicable to the present invention are not limited to those mentioned above. The charge-transporting substances can be used individually or as a mixture of two or more of them.

When a low molecular charge-transporting substance is used, the coating membrane can be formed by selecting a suitable binder. However, a high molecular charge-transporting substance having membrane-forming property may also be used. Further, it is also possible to mix the above-mentioned high molecular charge-transporting substance with the binder.

As the binder used here, the above-mentioned various resins used for the preparation of charge-generating layers can be used, and various solvents as described above are applicable as the solvent for binder.

The membrane thickness of the charge-transporting layer thus formed is 2-100 $\mu$m, preferably 5-30 $\mu$m.

As the undercoating layer 5, high molecular organic substances such as gelatin, casein, polyvinyl alcohol, ethyl cellulose, etc., aluminum oxide, and the like, may be used, besides the high molecular polymers used as the above-mentioned binder resin.

The photosensitive layer of the photosensitive members for electrophotography of the present invention may further contain one or two or more of electron accepting substances and coloring matters, for the purpose of improving sensibility, suppressing the elevation of residual electric potential and the fatigue, which appear on the repeated use, and the like.

As the electron accepting substances used here, there can be mentioned, for example, acid anhydrides such as succinic anhydride, maleic anhydride, phthalic anhydride, 4-chloronaphthalic anhydride, etc., cyano compounds such as tetracyanoethylene, terephthalmalononitrile, etc., aldehydes such as 4-nitrobenzaldehyde, etc., anthraquinones such as anthraquinone, 1-nitroanthraquinone, etc., polycyclic or heterocyclic nitro compounds such as 2,4,7-trinitrofluorenone, 2,4,5,7-tetranitrofluorenone, etc., and the like. They are used as chemical sensitizers.

As the coloring matters, those organic photoconductive compounds such as xanthene dyes, thiazine dyes, triphenylmethane dyes, quinoline pigments, copper phthalocyanine pigments, etc., are mentioned. They may be used as a kind of optical sensitizers.

Further, the photosensitive layer of the photosensitive members for electrophotography of the present invention may contain known plasticizers, for the purpose of improving molding characteristics, flexibility and mechanical strength. As the plasticizer, there can be mentioned dibasic acid esters, fatty acid esters, phosphoric acid esters, phthalic acid esters, chlorinated paraffins, epoxy-type plasticizers, and the like. The photosensitive layer may contain, if necessary, anti-oxidants, ultraviolet ray absorbing agents, and the like.

The invention is more concretely explained in the following, by giving Examples. However, the invention shall never be limited to those Examples.

EXAMPLE 1

In 200 ml of nitrobenzene, 0.762 g (3.2 m mol) of 1,2-diaminoanthraquinone was treated with 0.327 g (1.5 m mol) of pyromellitic anhydride at 210° C. for 24 hours while stirring. As the reaction proceeded, formation of precipitates was observed. Then, the precipitates were collected by filtration and washed 3 times with 500 ml each of tetrahydrofuran, 3 times with each of nitrobenzene, 3 times with 500 ml each of diethyl ether, and further 5 times with 2 l of acetone. The crystals thus obtained were dried at 60° C. under reduced pressure, whereby 0.74 g of a compound of the following formulae was obtained (yield: 65%):

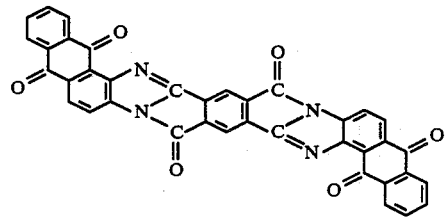
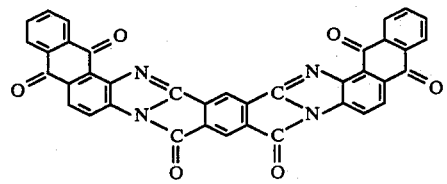

| Elementary analysis: | Calculated | Found |
|---|---|---|
| C(%) | 73.3 | 72.9 |
| H(%) | 2.3 | 2.4 |
| N(%) | 9.0 | 8.7 |

EXAMPLE 2

A dispersion obtained by dispersing 2 parts by weight of the imidazole compound No. 2, which was prepared from pyromellitic anhydride and the corresponding aromatic diamine in the same manner as Example 1 and 1 part by weight of a phenoxy resin (PKHH, from Union Carbide Corp.) in 8 parts by weight of dioxane for 12 hours by means of a ball mill disperser, was applied onto the surface of a PET coated with aluminum by vacuum evaporation (polyethylene terephthalate : Metalumy #100 from Toray Industries, Inc.) by means of a Baker applicator and dried at 80° C. for 1 hour, whereby a photosensitive member of the form shown in FIG. 1 having a photosensitive layer of 10 μm thick was prepared.

The photosensitive member thus prepared was corona electrified by means of an electrostatic paper analyzer, Model SP-428 from Kawaguchi Electric Co., Ltd. at +5KV in static mode and, after maintaining in dark place for 5 seconds, exposed at an illumination intensity of 5 lux, to investigate its electrification characteristics. As the electrification characteristics, initial electric potential ($V_0$), exposure amount necessary for attenuating the potential as attenuated in darkness for 5 seconds to the half ($E \frac{1}{2}$), residual potential at 5 seconds after the start of exposure ($V_R$) and charge retention coefficient as attenuated in darkness for 5 seconds ($V_K$) were measured. Further, in order to measure the fluctuation of potential between lightness and darkness as used repeatedly, the photosensitive member prepared in this Example was sticked on a cylinder of a simplified testing machine for electronic photography characteristics, which is provided with a corona electrifying instrument of +5KV, an optical system for exposure having an exposure amount of 10 lux·sec and an optical system for discharging exposure. Using this testing machine, the initial electric potential in lightness ($V_L$), the initial electric potential in darkness ($V_D$) and the potentials in lightness and darkness, $V_L$ and $V_D$, at the 1,000 th (1K) and 10,000 th (10K) repeated use, were measured.

EXAMPLES 3-5

Photosensitive members having the form shown in FIG. 2 were prepared according to the same manner as Example 2, except that each of the imidazole compounds shown in Tables 1 and 2 by compound numbers (synthesized each from pyromellitic anhydride and the corresponding aromatic diamine in the same manner as Example 1) was used instead of the imidazole compound No. 2 and, as the substrate, was used one prepared by forming an undercoating layer of vinyl chloride/vinyl acetate/maleic anhydride copolymer (Ethulek MF-10, from Sekisui Chemical Co., Ltd.) having a thickness of 0.05 μm on the PET coated with aluminum by vacuum evaporation which was used in Example 2. With these photosensitive members, the same measurements as Example 2 were effected. The results obtained are shown in Table 1 and Table 2.

TABLE 1

Results of measurements by means of the electrostatic paper analyzer

| Example | Imidazole compound No. | $V_0$ (V) | $E_{\frac{1}{2}}$ (lux · sec) | $V_R$ (V) | $V_K$ (%) |
|---|---|---|---|---|---|
| 2 | 2 | +380 | 10 | +9 | 89 |
| 3 | 10 | +393 | 17 | +16 | 91 |
| 4 | 15 | +351 | 13 | +13 | 87 |
| 5 | 18 | +372 | 14 | +13 | 85 |

TABLE 2

Results of evaluation of characteristics on repeated use

| | Initial | | 1 Kth | | 10 Kth | |
|---|---|---|---|---|---|---|
| Example | $V_D$ (V) | $V_L$ (V) | $V_D$ (V) | $V_L$ (V) | $V_D$ (V) | $V_L$ (V) |
| 2 | +380 | +35 | +375 | +44 | +360 | +53 |
| 3 | +393 | +59 | +378 | +68 | +361 | +82 |
| 4 | +351 | +43 | +345 | +57 | +339 | +74 |
| 5 | +372 | +51 | +360 | +60 | +352 | +75 |

EXAMPLE 6

A dispersion obtained by dispersing 2 parts by weight of the imidazole compound No. 3, which was prepared in the same manner as Example 1, 15 parts by weight of 2,4,7-trinitro-9-fluorenone and 15 parts by weight of a polycarbonate resin (Iupilon, from Mitsubishi Gas Chemical Company Inc.) in 188 parts by weight of dichloromethane for 12 hours by means of a ball mill disperser, was applied onto the surface of the PET coated with aluminum by vacuum evaporation (the same one as used in Example 2) by means of a Baker applicator and dried at 80° C. for 1 hour, whereby a photosensitive member of the form shown in FIG. 3 having a photosensitive layer of 20 μm thick was prepared. Then, the same measurements as Example 2 were effected, except that the corona electrification was performed at −5KV, instead of +5KV in Example 2, in the electrostatic copying test of the photosensitive member. The results obtained are shown in Tables 3 and 4, together with the results of the following Examples 7-9.

EXAMPLES 7-9

Photosensitive members having the form shown in FIG. 4 were prepared according to the same manner as Example 6, except that each of the imidazole compounds shown in Tables 3 and 4 by compound numbers (synthesized each from the corresponding starting materials in the same manner as Example 1) was used instead of the imidazole compound No. 3 and, as the substrate, was used one prepared by forming an undercoating layer of a vinyl chloride/vinyl acetate/maleic anhydride copolymer (Ethulek MF-10, from Sekisui Chemical Co., Ltd.) having a thickness of 0.05 μm on the PET coated with aluminum by vacuum evaporation which was used in Example 6. With these photosensitive members, the same measurements as Example 6 were effected. The results obtained are shown in Table 3 and Table 4.

TABLE 3

Results of measurements by means of the electrostatic paper analyzer

| Example | Imidazole compound No. | $V_0$ (V) | $E_{\frac{1}{2}}$ (lux · sec) | $V_R$ (V) | $V_K$ (%) |
|---|---|---|---|---|---|
| 6 | 3 | −405 | 10 | −11 | 87 |
| 7 | 11 | −387 | 12 | −15 | 85 |
| 8 | 13 | −400 | 15 | −18 | 90 |
| 9 | 16 | −392 | 14 | −16 | 82 |

TABLE 4

Results of evaluation of characteristics on repeated use

| | Initial | | 1 Kth | | 10 Kth | |
|---|---|---|---|---|---|---|
| Example | $V_D$ (V) | $V_L$ (V) | $V_D$ (V) | $V_L$ (V) | $V_D$ (V) | $V_L$ (V) |
| 6 | −405 | −41 | −395 | −46 | −390 | −55 |
| 7 | −387 | −47 | −376 | −55 | −359 | −70 |
| 8 | −400 | −62 | −392 | −77 | −378 | −88 |
| 9 | −392 | −55 | −379 | −62 | −360 | −73 |

EXAMPLE 10

A dispersion obtained by dispersing 2 parts by weight of the imidazole compound No. 1 prepared in Example 1 and 1 part by weight of a phenoxy resin (the same one as used in Example 2) in 97 parts by weight of 1,4-dioxane for 12 hours by means of a ball mill disperser, was applied onto the same PET coated with aluminum by vacuum evaporation as used in Example 2 by means of a Baker applicator and dried at room temperature for 1 hour, whereby a charge-generating layer of 0.5 μm thick was formed.

Next, 1 part by weight of a hydrazone series compound represented by the following formula,

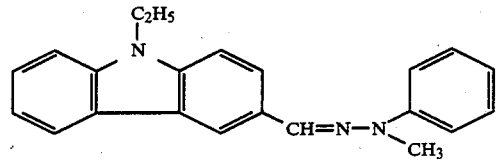

1 part by weight of a polycarbOnate resin (the same one as used in Example 6) and 8 parts by weight of dichloromethane were mixed together and dissolved by stirring with a stirrer. The solution thus obtained was applied onto the charge-generating layer by means of a Baker applicator and then dried at 80° C. for 1 hour, whereby a photosensitive member of the form shown in FIG. 5 having a photosensitive layer of 20 μm thick was prepared. The same measurements as Example 6 were effected with regard to this photosensitive member. The results obtained are shown in Tables 5 and 6, together with the results of the following Examples 11-13.

EXAMPLES 11-13

Figure 6:
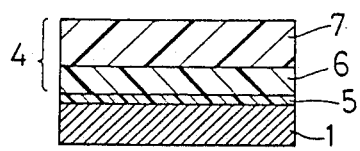

Photosensitive members having the form shown in FIG. 6 were prepared according to the same manner as Example 10, except that each of the imidazole compounds shown in Tables 5 and 6 by compound numbers (synthesized each from the corresponding starting materials in the same manner as Example 1) was used instead of the imidazole compound No. 1 and, as the substrate, was used one prepared by forming an undercoating layer of a vinyl chloride/vinyl acetate/maleic anhydride copolymer (Ethulex MF-10, from Sekisui Chemical Co., Ltd.) having a thickness of 0.05 μm on the PET coated with aluminum by vacuum evaporation which was used in Example 10. With regard to these photosensitive members, the same measurements as Example 10 were effected. The results obtained are shown in Table 5 and Table 6.

TABLE 5

| | Results of measurements by means of the electrostatic paper analyzer | | | | |
|---|---|---|---|---|---|
| Example | Imidazole compound No. | $V_0$ (V) | $E_{\frac{1}{2}}$ (lux·sec) | $V_R$ (V) | $V_K$ (%) |
| 10 | 1 | −690 | 7 | −8 | 90 |
| 11 | 9 | −720 | 12 | −12 | 87 |
| 12 | 17 | −703 | 13 | −14 | 92 |
| 13 | 18 | −711 | 9 | −9 | 90 |

TABLE 6

| | Results of evaluation of characteristics on repeated use | | | | | |
|---|---|---|---|---|---|---|
| | Initial | | 1 Kth | | 10 Kth | |
| Example | $V_D$ (V) | $V_L$ (V) | $V_D$ (V) | $V_L$ (V) | $V_D$ (V) | $V_L$ (V) |
| 10 | −690 | −25 | −685 | −28 | −678 | −33 |
| 11 | −720 | −42 | −710 | −51 | −695 | −58 |
| 12 | −703 | −50 | −695 | −59 | −680 | −73 |
| 13 | −711 | −36 | −700 | −43 | −693 | −51 |

EXAMPLE 14

One part by weight of a hydrazone series compound represented by the following formula,

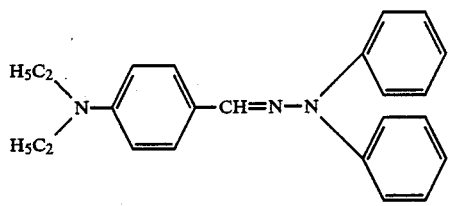

1 part by weight of a polycarbonate resin (the same one as used in Example (6) and 8 parts by weight of dichloromethane were mixed together and dissolved by stirring with a stirrer. The solution thus obtained was applied onto the PET coated with aluminum by vacuum evaporation (the same one as used in Example (2), by means of a Baker applicator, and dried at 80° C. for 1 hour, whereby a charge-transporting layer having a membrane thickness of 19.5 μm was formed.

Figure 7:
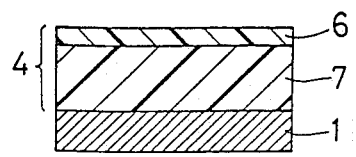

Next, a dispersion obtained by dispersing 2 parts by weight of the imidazole compound No. 5 and 1 part by weight of a phenoxy resin (the same one as used in Example 2) in 97 parts by weight of 1,4-dioxane for 12 hours by means of a ball mill disperser, was applied onto the charge-transporting layer by means of a Baker applicator and then dried at 80° C. for 1 hour, whereby a photosensitive member of the form shown in FIG. 7 having a photosensitive layer of 20 μm thick was prepared. With regard to this photosensitve member, the same measurements as Example 2 were effected. The results obtained are shown in Table 7 and Table 8, together with the results of the following Examples 15-17.

EXAMPLES 15-17

Figure 8:
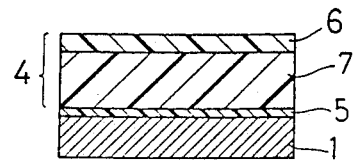

Photosensitive members having the form shown in FIG. 8 were prepared according to the same manner as Example 14, except that each of the imidazole compounds shown in Tables 7 and 8 by compound numbers (synthesized each from the corresponding starting materials in the same manner as Example 1) was used instead of the imidazole compound No. 5 and, as the substrate, was used one prepared by forming an undercoating layer of a vinyl chloride/vinyl acetate/maleic anhydride copolymer (Ethulex MF-10, from Sekisui Chemical Co., Ltd.) having a thickness of 0.05 μm on the PET coated with aluminum by vacuum evaporation which was used in Example 14. With regard to these photosensitive members, the same measurements as Example 14 were effected. The results obtained are shown in Table 7 and Table 8.

TABLE 7

| | Results of measurements by means of the electrostatic paper analyzer | | | | |
|---|---|---|---|---|---|
| Example | Imidazole compound No. | $V_0$ (V) | $E_{\frac{1}{2}}$ (lux·sec) | $V_R$ (V) | $V_K$ (%) |
| 14 | 5 | +730 | 9 | +15 | 88 |
| 15 | 6 | +704 | 14 | +20 | 89 |
| 16 | 7 | +720 | 12 | +19 | 89 |
| 17 | 8 | +695 | 9 | +16 | 86 |

TABLE 8

| | Results of evaluation of characteristics on repeated use | | | | | |
|---|---|---|---|---|---|---|
| | Initial | | 1 Kth | | 10 Kth | |
| Example | $V_D$ (V) | $V_L$ (V) | $V_D$ (V) | $V_L$ (V) | $V_D$ (V) | $V_L$ (V) |
| 14 | +730 | +39 | +722 | +45 | +708 | +53 |
| 15 | +704 | +60 | +690 | +72 | +682 | +80 |
| 16 | +720 | +55 | +713 | +63 | +708 | +72 |
| 17 | +695 | +42 | +690 | +50 | +683 | +60 |

COMPARATIVE EXAMPLE 1

A photosensitive member was prepared according to the same manner as Example 2, except that a polycyclic guinone series pigment (Monolite Red 2Y, from I.C.I. Ltd.) of the formula

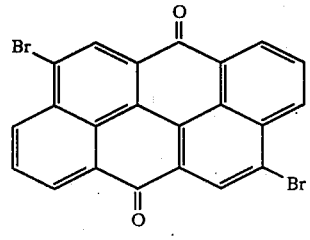

was used instead of the imidazole compound No. 2. Then, the same measurements as Example 2 were effected with regard to the photosensitive member. The results obtained are shown in Tables 9 and 10.

COMPARATIVE EXAMPLE 2

A photosensitive member was prepared according to the same manner as Example 3, except that a quinacridone sereis pigment (Cinquasia Red Y RT-759-D, from Ciba-Geigy Ltd.) of the formula

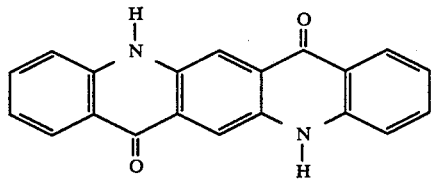

was used instead of the imidazole compound No. 10. The same measurements as Example 3 were effected with regard to the photosensitive member. The results obtained are shown in Tables 9 and 10.

COMPARATIVE EXAMPLE 3

A photosensitive member was prepared according to the same manner as Example 6, except that an isoindolinone series pigment (Irgazin Yellow 2RLT, from Ciba-Geigy Ltd.) of the formula

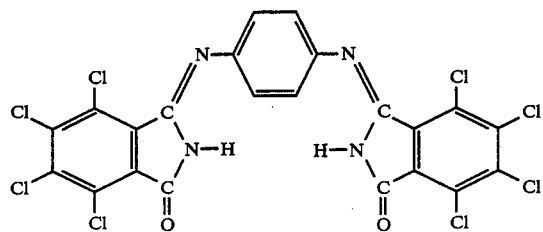

was used instead of the imidazole compound No. 3. The same measurements as Example 6 were effected with regard to the photosensitive member. The results obtained are shown in Tables 9 and 10.

COMPARATIVE EXAMPLE 4

A photosensitive member was prepared according to the same manner as Example 7, except that an indigo series pigment (Vat Blue 1, from Mitsui Toatsu Dyestuff Inc.) of the formula

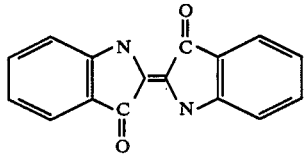

was used instead of the imidazole compound No. 11. The same measurements as Example 7 were effected with regard to the photosensitive member. The results obtained are shown in Tables 9 and 10.

COMPARATIVE EXAMPLE 5

A photosensitive member was prepared according to the same manner as Example 10, except that a thioinidigo series pigment (Vat Red 41, from Mitsui Toatsu Dyestuff Inc.) of the formula

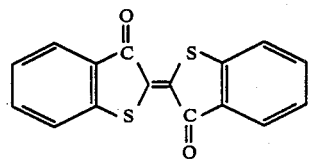

was used instead of the imidazole compound No. 1. The same measurements as Example 10 were effected with regard to the photosensitive member. The results obtained are shown in Table 9 and 10.

COMPARATIVE EXAMPLE 6

A photosensitive member was prepared according to the same manner as Example 12, except that a xanthene series dyestuff (Eosine Y) of the formula

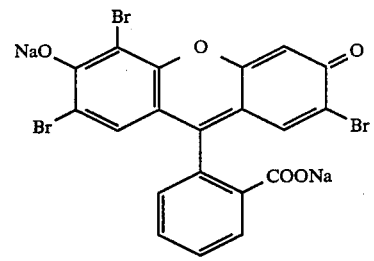

was used instead of the imidazole compound No. 17. The same measurements as Example 12 were effected with regard to the photosensitive member. The results obtained are shown in Tables 9 and 10.

COMPARATIVE EXAMPLE 7

A photosensitive member was prepared according to the same manner as Example 14, except that an acridine series dyestuff (Acridine Yellow, from Chroma Ltd.) of the formula

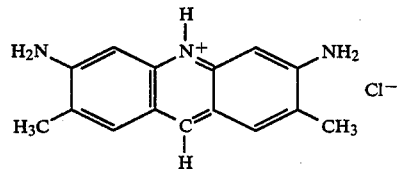

was used instead of the imidazole compound No. 5. The same measurements as Example 16 were effected with regard to the photosensitive member. The results obtained are shown in Tables 9 and 10.

COMPARATIVE EXAMPLE 8

A photosensitive member was prepared according to the same manner as Example 17, except that a triphenylmethane series dyestuff (Ethylviolet) of the formula

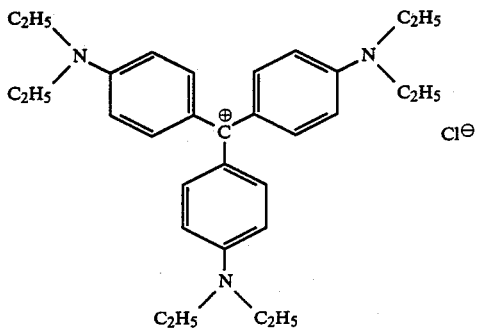

was used instead of the imidazole compound No. 8. The same measurements as Example 17 were effected with regard to the photosensitive member. The results obtained are shown in Tables 9 and 10.

TABLE 9

Results of measurements by means of the electrostatic paper analyzer

| Comparative Example | $V_0$ (V) | $E_{\frac{1}{2}}$ (lux · sec) | $V_R$ (V) | $V_K$ (%) |
|---|---|---|---|---|
| 1 | +200 | 54 | +45 | 80 |
| 2 | +300 | 39 | +55 | 75 |
| 3 | −365 | 89 | −50 | 70 |
| 4 | −390 | 32 | −60 | 75 |
| 5 | −400 | 40 | −30 | 80 |
| 6 | −405 | 33 | −35 | 81 |
| 7 | +355 | 45 | +40 | 76 |
| 8 | +370 | 42 | +45 | 77 |

TABLE 10

Results of evaluation of characteristics on repeated use

| Comparative Example | Initial | | 1 Kth | | 10 Kth | |
|---|---|---|---|---|---|---|
| | $V_D$ (V) | $V_L$ (V) | $V_D$ (V) | $V_L$ (V) | $V_D$ (V) | $V_L$ (V) |
| 1 | +200 | +45 | +180 | +60 | +165 | +90 |
| 2 | +300 | +55 | +270 | +70 | +240 | +105 |
| 3 | −365 | −50 | −350 | −65 | −325 | −75 |
| 4 | −390 | −60 | −370 | −75 | −330 | −90 |
| 5 | −400 | −30 | −390 | −40 | −360 | −55 |
| 6 | −405 | −35 | −390 | −50 | −335 | −70 |
| 7 | +355 | +40 | +330 | +60 | +305 | +90 |
| 8 | +370 | +45 | +340 | +65 | +310 | +100 |

What is claimed is:

1. A photosensitive member comprising a photosensitive layer on a conductive support, said photosensitive layer containing a compound of the group of 1,2,4,5-Benzoylenebis(anthraquinone(1,2-D)imidazole) compounds represented by the following general formulas (1) or (2):

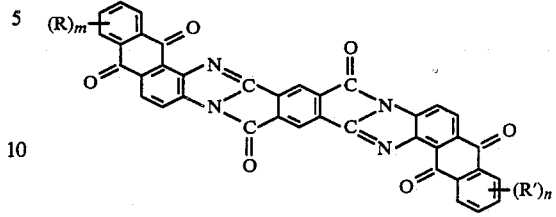

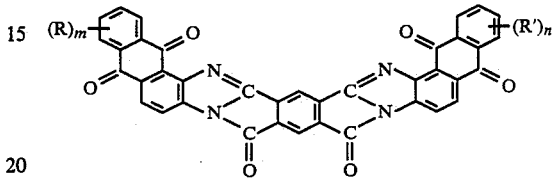

wherein R and R' each are a hydrogen atom, a halogen atom, an hydroxyl group, a lower alkyl group, a lower alkoxy group or an aryl group which may be substituted and m and an each are an integer of 1 or 2.

2. The photosensitive member of claim 1, wherein the photosensitive layer is a multilayer type, comprising a charge-generating layer and a charge-transporting layer, said charge-generating layer containing the imidazole compound of general formulas (1) or (2).

3. The photosensitive member of claim 2, wherein the charge-generating layer is formed to 0.02–20 μm thickness.

4. The photosensitive member of claim 2, wherein the charge-transporting layer is formed to 2–100 μm thickness.

5. The photosensitive member of claim 3, wherein the charge-transporting layer is formed to 2–100 μm thickness.

6. The photosensitive member of claim 2, wherein R and R' are each a hydrogen atom.

7. The photosensitive member of claim 2, wherein R and R' are each a halogen atom.

8. The photosensitive member of claim 2, wherein the lower alkyl group is a methyl or ethyl group.

9. The photosensitive member of claim 2, wherein the lower alkoxy group is a methoxy or ethoxy group.

10. The photosensitive member of claim 2, wherein the aryl group which may be substituted is a phenyl group which may be substituted with a halogen atom, a lower alkyl group, a lower alkoxy group, a nitro group or a cyano group.

* * * * *